United States Patent
Coughlin

(10) Patent No.: US 10,011,626 B2
(45) Date of Patent: Jul. 3, 2018

(54) METHOD FOR THE PURIFICATION OF DECITABINE

(71) Applicant: Johnson Matthey Public Limited Company, London (GB)

(72) Inventor: Daniel James Coughlin, Mullica Hill, NJ (US)

(73) Assignee: Johnson Matthey Public Limited Company, London (GB)

( * ) Notice: Subject to any disclaimer, the term of this patent is extended or adjusted under 35 U.S.C. 154(b) by 149 days.

(21) Appl. No.: 15/053,549

(22) Filed: Feb. 25, 2016

(65) Prior Publication Data

US 2016/0168182 A1 Jun. 16, 2016

Related U.S. Application Data

(62) Division of application No. 14/041,562, filed on Sep. 30, 2013, now abandoned.

(60) Provisional application No. 61/708,289, filed on Oct. 1, 2012.

(51) Int. Cl.
 *C07H 1/06* (2006.01)
 *C07H 19/12* (2006.01)

(52) U.S. Cl.
 CPC .............. *C07H 1/06* (2013.01); *C07H 19/12* (2013.01)

(58) Field of Classification Search
 None
 See application file for complete search history.

(56) References Cited

U.S. PATENT DOCUMENTS

| 2006/0014949 A1 | 1/2006 | Redkar et al. |
| 2010/0087637 A1 | 4/2010 | Henschke et al. |
| 2012/0046457 A1 | 2/2012 | Kolla et al. |

FOREIGN PATENT DOCUMENTS

| WO | WO 2006/017278 A1 | 2/2006 | |
| WO | WO2010/129211 | 11/2010 | |
| WO | WO 2010/129211 A2 | 11/2010 | |
| WO | WO-2010129211 A2 * | 11/2010 | ........... C07D 251/16 |
| WO | WO 2011/040984 A1 | 4/2011 | |

OTHER PUBLICATIONS

International Search Report for International Application No. PCT/IB2013/002162 dated Dec. 12, 2013 and Written Opinion.

* cited by examiner

*Primary Examiner* — Traviss C McIntosh, III
(74) *Attorney, Agent, or Firm* — Shanay M. McCastle

(57) ABSTRACT

A method of preparing purified decitabine comprises mixing crude decitabine with solvent, such as dimethylacetamide, to form a solution or suspension and forming the purified decitabine from the solution or suspension. The forming step comprises adding an anti-solvent, such as ethanol, to the solution or suspension. The forming step may further comprise after adding ethanol to provide a mixture of dimethylacetamide and ethanol: cooling the mixture; isolating the solid decitabine present in the cooled mixture; and evaporating residual dimethylacetamide and ethanol from the solid decitabine to provide the purified decitabine. The mixture of dimethylacetamide and ethanol may be heated. The purification method preferably results in decitabine having a ratio of the β-anomer of decitabine to the α-anomer of decitabine of at least about 99.9:0.1.

20 Claims, No Drawings

METHOD FOR THE PURIFICATION OF DECITABINE

This application is a divisional of U.S. patent application Ser. No. 14/041,562, filed Sep. 30, 2013, which claims the benefit of U.S. Patent Application No. 61/708,289, filed Oct. 1, 2012, the disclosures of which are incorporated herein by reference in their entirety for all purposes.

FIELD OF THE INVENTION

This invention pertains to the purification of decitabine.

BACKGROUND OF THE INVENTION

The drug compound having the adopted name "decitabine" has chemical names: 4-amino-1-(2-deoxy-β-D-erythropentofuranosyl)-1,3,5-triazin-2-(1H)-one; or 5-aza-2'-deoxy cytidine; and is structurally represented by formula (I).

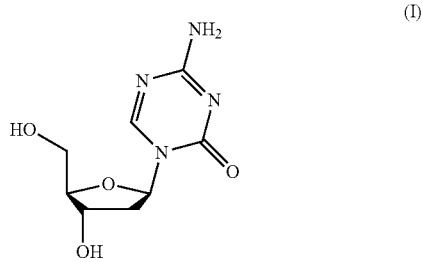

Decitabine, a pyrimidine nucleoside analog of cytidine, is used for treating patients with myelodysplastic syndromes (MDS) including previously treated and untreated, de novo and secondary MDS of all French-American-British subtypes (refractory anemia, refractory anemia with ringed sideroblasts, refractory anemia with excess blasts, refractory anemia with excess blasts in transformation, and chronic myelomonocytic leukemia) and intermediate-1, intermediate-2, and high-risk International Prognostic Scoring System groups.

Decitabine is the active ingredient in the commercially marketed product DACOGEN®, in the form of a sterile lyophilized powder for injection.

U.S. Patent Application Publication No. 2006/0014949 discloses pharmaceutical compositions and methods for treatment of neoplastic conditions using polymorphs of decitabine. This publication also discloses methods for manufacturing and administering such pharmaceutical compositions. This publication also discloses that two anomeric forms of decitabine can be distinguished, wherein the β-anomer is the active form of decitabine. The publication mentions various modes of decomposition of decitabine in aqueous solution, namely: (a) conversion of the active β-anomer to the inactive α-anomer; (b) ring cleavage of the aza-pyrimidine ring to form N-(formylamidino)-N'-beta-D-2'-deoxy-(ribofuranosy)-urea; and (c) subsequent forming of guanidine compounds.

U.S. Patent Application Publication No. 2010/0087637 discloses a method for producing a β-enriched protected decitabine comprising: a) coupling a protected 2-deoxy-ribofuranose with a protected 5-azacytosine in the presence of a catalyst to form a reaction mixture comprising a protected decitabine; and b) quenching the reaction mixture of step a) with a base. The publication discloses that the ratio of the undesired α-anomer to the desired β-anomer of the protected decitabine precursor is dynamic both under the reaction conditions of the anomers formed and also during the work-up process, specifically due to epimerisation of the carbohydrate C1 chiral center formed in the coupling reaction. The undesired α-anomer was found to become enriched following its formation by this epimerisation. The α-anomer was found to be the thermodynamically favored isomer. This publication discloses a method to avoid the undesired enrichment of the α-anomer, to maintain the relative and absolute amounts of the β-anomer initially formed in the coupling reaction.

U.S. Patent Application Publication No. 2012/0046457 discloses processes for the preparation and purification of decitabine and processes for the preparation of a crystalline form of decitabine. The publication discloses a process for purifying decitabine comprising first providing a solution of decitabine in dimethylsulphoxide and then crystallizing a solid from the solution of decitabine and dimethylsulphoxide. Crystallizing can be achieved by combining an anti-solvent with the solution. Such anti-solvents include an alcohol, an ester, or any mixture thereof, and the anti-solvent in one embodiment is a mixture of methanol and ethyl acetate.

SUMMARY OF THE INVENTION

It is highly desirable to provide decitabine which is substantially pure and, in particular, has a high ratio of the β-anomer to the α-anomer of decitabine. In fact, according to a guideline issued by the International Conference on Harmonization (ICH), the weight ratio of the β-anomer to the α-anomer of decitabine ("the beta-to-alpha anomer ratio") must be greater than 99.85:0.15. Accordingly, there is a need to provide a method for purifying crude decitabine and, in particular, to provide decitabine with a beta-to-alpha anomer ratio of above 99.85:0.15, and more preferably above 99.9:0.1.

In view of these and other purposes, the present invention is directed to a method of purifying crude decitabine and the decitabine made thereby. The method of preparing purified decitabine comprises:

a. mixing crude decitabine with dimethylacetamide to form a solution or suspension; and;

b. forming the purified decitabine as a solid product from the solution or suspension of step a).

In an embodiment, the step of forming the purified decitabine from the solution or suspension comprises adding an anti-solvent, such as ethanol, to the solution or suspension. The forming step may further comprise, after adding ethanol to provide a mixture of dimethylacetamide and ethanol: cooling the mixture of dimethylacetamide and ethanol to provide a cooled mixture; isolating the solid decitabine present in the cooled mixture; and evaporating residual dimethylacetamide and ethanol from the solid decitabine to provide the purified decitabine.

It is to be understood that both the foregoing general description and the following detailed description are exemplary, but are not restrictive, of the invention.

DETAILED DESCRIPTION OF THE INVENTION

Several considerations were taken into account in developing a method for purifying decitabine. First, decitabine is not soluble in many solvents. As mentioned in the '949 Publication, decitabine is generally poorly soluble in many solvents. A notable exception is methyl sulfoxide, in which the compound was found to be soluble to the extent of approximately 37 mg/mL. Decitabine is also slightly soluble in 1,1,1,3,3,3-hexafluoro-2-propanol (about 18 mg/mL) and sparingly soluble in water (about 8 mg/mL). Moreover, it was found that it was undesirable to use large volumes of solvent for reasons of expense and process capacity. Furthermore, it was found that the inclusion of water in the process, especially at high temperatures, causes degradation of decitabine, particularly by causing hydrolysis. As stated in the '637 published application, decitabine exists as the α-anomer and the β-anomer, and the β-anomer is desired but the α-anomer is the thermodynamically favored isomer.

With all of this in mind, a process for purifying decitabine was developed. The process comprises: a) mixing crude decitabine with a solvent, such as dimethylacetamide, to form a solution or suspension; and b) forming the purified decitabine as a solid product from the solution or suspension of step a). In an embodiment, the step of forming the purified decitabine from the solution or suspension comprises adding an anti-solvent, such as ethanol, to the solution or suspension. The forming step may further comprise, after adding ethanol to provide a mixture of dimethylacetamide and ethanol: cooling the mixture of dimethylacetamide and ethanol to provide a cooled mixture; isolating the solid decitabine present in the cooled mixture; and evaporating residual dimethylacetamide and ethanol from the solid decitabine to provide the purified decitabine. The purification method results in a purified decitabine product having a beta-to-alpha anomer ratio of at least 99.9:0.1 when the beta-to-alpha anomer ratio of the crude decitabine is preferably between about 90:10 to about 99:1, and more preferably between about 95:5 to about 99:1. The purification method of the invention improves the beta-to-alpha anomer ratio regardless of the beta-to-alpha anomer ratio of the crude decitabine, but is especially advantageous when the beta-to-alpha anomer ratio of the crude decitabine is less than about 99.5:0.5 and preferably less than about 99:1. As used herein, the purity values are in terms of area under a chromatographic curve (AUC) and purity was measured by HPLC assay.

In carrying out the method for preparing purified decitabine, first crude decitabine is mixed with a solvent, such as dimethylacetamide, to form a solution or a suspension. The solvent selected can be any known suitable solvent having an adequate solubility for decitabine. Preferably, decitabine is at least moderately soluble in the solvent used to avoid using too much solvent. It has been found that preferably aprotic amide solvents are used, such as dimethylacetamide, dimethyl formamide (DMF), and/or N-methylpyrrolidinone (NMP).

The crude decitabine used in this step may be from any source. Typically, such crude decitabine has a beta-to-alpha anomer ratio of between about 99:1 and 95:5 and more typically about 99:1. Exemplary methods for synthesizing decitabine may be found in U.S. Patent Publication Nos. 2010/0087637 and 2012/0046457.

In one embodiment, crude decitabine is partially dissolved in a solvent, such as dimethylacetamide, at room temperature and the mixture is heated until complete dissolution of the decitabine or to a temperature above the point at which the decitabine is fully dissolved. Certain non-decitabine components or impurities may remain undissolved. In one embodiment, crude decitabine from any suitable synthesis process, such as those described above, is first suspended in dimethylacetamide to form a mixture. Relative amounts of decitabine and dimethylacetamide may be used such that the amount of decitabine is above the solubility limit at the temperature in which the mixture is formed. Then, the mixture may be heated to a temperature such that the decitabine completely dissolves or to a temperature above that temperature. Preferably, the heating of the mixture of the suspension of crude decitabine and dimethylacetamide is to a temperature of from about 55° C. to about 70° C. for a time of from about 10 to about 30 minutes. The time and temperature should be selected to ensure that the decitabine is preferably fully dissolved. Alternatively, an amount of solvent may be used such that the decitabine fully dissolves in the solvent at the temperature of mixing (e.g., room temperature). Then, the solution may be filtered to remove insoluble impurities, such as non-decitabine components or impurities, and the filtrate may again be heated and stirred if necessary to ensure that the decitabine is fully dissolved.

The process next involves forming the purified decitabine from the solution or suspension produced by the mixing step. This forming step may involve adding an anti-solvent to the solution or suspension. The anti-solvent used can be any suitable anti-solvent known in the art to aid in forming solid decitabine from a mixture of decitabine and dimethylacetamide. Such anti-solvents may include methanol, isopropanol, ethyl acetate, acetone, methyl ethyl ketone, and acetonitrile, but preferably the anti-solvent is ethanol. The amount of anti-solvent used is preferably an amount sufficient to form solid decitabine, upon cooling, of at least 50%, or at least 80% of the decitabine added as crude decitabine. In a system in which ethanol is used as the anti-solvent and dimethylacetamide is used as the solvent, the amount of ethanol added may be about 70% to about 85% v/v, more preferably about 75% to about 78% v/v. As used herein, the term "% v/v" refers to the percent by volume of the identified solvent based on the sum of the pre-mixed individual volumes of all of the solvents and anti-solvents. In an embodiment in which ethanol is used as the anti-solvent and dimethylacetamide is used as the solvent, it has been found that the solution prior to addition of the ethanol becomes cloudy upon addition of ethanol.

The product formed after adding the anti-solvent may optionally be heated prior to a cooling step, discussed below. It has been found that, in an embodiment in which ethanol is used as the anti-solvent and dimethylacetamide is used as the solvent, the solution remains cloudy during the heating. In this embodiment of the invention, the heating of the product after adding ethanol may be for a time of about 10 to about 90 min at a temperature of from about 50° C. to about 75° C., preferably for a time of from about 30 to about 60 min at a temperature of from about 60° C. to about 70° C.

As mentioned above, the forming step may further comprise, after adding ethanol to provide a mixture of dimethylacetamide and ethanol, cooling the mixture of dimethylacetamide and ethanol to provide a cooled mixture and to form solid decitabine. Cooling causes solid decitabine to drop out of the solution. It is believed that the α-anomer is more soluble in this solution than the β-anomer, thereby leading to a solid decitabine product which is more pure (i.e., has a higher beta-to-alpha anomer ratio). Preferably, the cooling step comprises cooling the product, either directly after the addition of ethanol or after the optional heating step, to a temperature of from about 0° C. to about 20° C., more preferably, from about 5° C. to about 15° C.

Thereafter, the forming step may involve isolating solid decitabine present in the cooled mixture from the solvent system. This may include filtering the solid decitabine from the solvent system. Any known filtering system known in the art may be used for this purpose, such as Buchner filter funnels or other filtration/collection apparatus.

Next, the final part of the forming step may involve evaporating the solvent. In particular, any residual solvent is evaporated from the product of the isolation step to form the purified decitabine. This may, for example, involve exposing the product to a reduced pressure by applying vacuum. In addition, the product after the filtering step may be rinsed with a solvent prior to performing the evaporating step. Preferably, that solvent is ethanol. In sum, the evaporating step is done to dry any residual solvent from the product and may include drying for a period of 24 hours or more, which provides the purified decitabine as a solid product.

Preferably, the entire method is run such that the temperature of the process never exceeds 80° C., more preferably not exceeding 70° C. Even more preferably, the addition of or exposure to water is avoided in order to limit the degradation of decitabine by hydrolysis. The method of the present invention is capable of providing decitabine with a beta-to-alpha anomer ratio of at least 99.9:0.1. In addition, the decitabine content of the purified product, as purified according to the steps discussed below in the examples, was at least 99%.

EXAMPLE

The following example is included to more clearly demonstrate the overall nature of the present invention.

Solid crude decitabine (1.0 g) was partially dissolved in dimethylacetamide (10 mL, Sigma-Aldrich, Fluka, 44901-1L) and the mixture was then heated in a bath set at 65° C. The decitabine in the solid crude decitabine was dissolved completely when the bath temperature reached 38° C., although certain less soluble non-decitabine components and impurities remained in solid form. The solution was filtered through a 0.45 pm syringe filter (PTFE) to remove the non-decitabine components and impurities, and the filter was rinsed with dimethylacetamide (1 mL). The filtrate was heated and stirred at 55° C., which was the bath temperature. Ethanol (35 mL, 200 proof, 99.5%) at room temperature was added slowly, while keeping the temperature of the mixture between 40-55° C., and the solution became cloudy upon addition of ethanol After the ethanol addition was completed, the mixture was heated to 65° C. and maintained at this temperature for approximately 30 min. The mixture was then gradually cooled to room temperature with stirring, then to 7° C.

Solid cake product was filtered in a glove bag under nitrogen. The cake was washed with anhydrous ethanol (3×3mL) and dried under vacuum on the filter in a glove bag for 15 min. Then, the solid was transferred to a vial and dried at reduced pressure (about 6 mm Hg) for 18 hours at ambient temperature to give 0.81 grams of purified decitabine (81% recovery) as a solid product. The isomeric purity was 99.9% AUC of the desired β-anomer (i.e., the purified product had a beta-to-alpha anomer ratio of 99.9:0.1), and the solid form matched a decitabine standard (from methanol crystallization) by XRPD, having XRPD peaks located approximately at 7.1, 12.9, 14.2, 18.9, 21.3, 23.8, 24.8 and 26.6±0.2° 2Θ.

Residual ethanol content by GC with headspace analysis (Agilent Technologies GC Model #7890 with headspace attachment Model #G1888) after drying under vacuum of around 6 mm Hg at 22° C. for 24 hours was 3960 ppm (ICH limit 5000 ppm), and residual dimethylacetamide was non-detectable.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method of preparing purified decitabine, comprising:
   a) mixing crude decitabine with dimethylacetamide to form a solution or suspension; and
   b) forming the purified decitabine as a solid product from the solution or suspension of step a).

2. The method of claim 1, wherein step b) comprises adding ethanol to the solution or suspension.

3. The method of claim 2, wherein step b) further comprises, after adding ethanol to provide a mixture of dimethylacetamide and ethanol:
   cooling the mixture of dimethylacetamide and ethanol to provide a cooled mixture;
   isolating solid decitabine present in the cooled mixture; and
   evaporating residual dimethylacetamide and ethanol from the solid decitabine to provide the purified decitabine.

4. The method of claim 3, further comprising, between the steps of adding ethanol and cooling, heating the mixture of dimethylacetamide and ethanol.

5. The method of claim 4, wherein the heating step comprises heating the mixture of dimethylacetamide and ethanol to a temperature of from about 50° C. to about 75° C. and maintaining for a time of about 10 to about 90 min.

6. The method of claim 4, wherein the heating step comprises heating the mixture of dimethylacetamide and ethanol to a temperature of from about 60° C. to about 70° C. and maintaining for a time of from about 30 to about 60 min.

7. The method of claim 1, wherein the temperature of the process does not exceed 80° C.

8. The method of claim 1, wherein the temperature of the process does not exceed 70° C.

9. The method of claim 1, wherein the mixing step comprises suspending the crude decitabine in dimethylacetamide to form a mixture of crude decitabine and dimethylacetamide and heating the mixture of crude decitabine and dimethylacetamide to a temperature sufficient to dissolve the crude decitabine.

10. The method of claim 9, wherein heating the mixture of crude decitabine and dimethylacetamide comprises heating to a temperature of from about 55° C. to about 70° C. for a time of from about 10 to about 30 min.

11. The method of claim 2, wherein the amount of ethanol added comprises from about 70% to about 85% v/v.

12. The method of claim 2, wherein the amount of ethanol added comprises from about 75% to about 78% v/v.

13. The method of claim 3, wherein the cooling step comprises cooling the mixture of dimethylacetamide and ethanol to a temperature of from about 0° C. to about 20° C.

14. The method of claim 1, wherein the cooling step comprises cooling the mixture of dimethylacetamide and ethanol to a temperature of from about 5° C. to about 15° C.

15. The method of claim 3, wherein isolating the solid decitabine comprises filtering.

16. The method of claim 3, wherein evaporating comprises applying vacuum to the solid decitabine.

17. The method of claim 3, further comprising rinsing the solid decitabine with a solvent after the isolating step and before the evaporating step.

18. The method of claim 17, wherein the solvent is ethanol.

19. A method of preparing purified decitabine, comprising
   a) mixing crude decitabine with dimethylacetamide to form a solution or suspension;
   b) adding ethanol to the solution or suspension in an amount from about 70% to about 85% v/v;
   c) cooling the product of step b) to a temperature of between about 5° C. to about 15° C. to provide a cooled mixture;
   d) isolating solid decitabine present in the cooled mixture; and
   e) evaporating residual dimethylacetamide and ethanol from the solid decitabine to provide the purified decitabine,
   wherein the temperature of the process throughout does not exceed 80° C.

20. The method of claim 19, further comprising, between steps b) and c), heating the mixture of dimethylacetamide and ethanol for a time of between 30 and 60 min and at a temperature of between 60° C. and 70° C.

\* \* \* \* \*